United States Patent
Richards et al.

Patent Number: 6,126,671
Date of Patent: *Oct. 3, 2000

[54] GRASPING DEVICES AND ARTICLES

[75] Inventors: Theresa Richards, Fitchburg, Mass.; Frank Bimbo, Peterborough, N.H.

[73] Assignee: TFX Medical, Incorporated, Jaffrey, N.H.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/852,633

[22] Filed: May 7, 1997

Related U.S. Application Data

[63] Continuation-in-part of application No. 08/726,617, Oct. 7, 1996, abandoned.

[51] Int. Cl.[7] .................. A61B 17/00; A41D 19/00; A43B 23/28
[52] U.S. Cl. .................. 606/190; 606/207; 2/161.8; 2/161.7; 36/59 R
[58] Field of Search .................. 600/190, 192, 600/210; 606/190, 205, 207; 2/159, 161.1, 161.2, 161.3, 161.7, 161.8; 273/81 R, 165, 166, 81.6, 81 B; 36/7.7, 7.1 R, 59 R, 61, 62, 59 C; 128/849

[56] References Cited

U.S. PATENT DOCUMENTS

| | | |
|---|---|---|
| 273,382 | 3/1883 | Packham . |
| 427,555 | 5/1890 | Connor . |
| 1,422,538 | 7/1922 | Cameron . |
| 2,015,617 | 9/1935 | Claudius . |
| 2,121,989 | 6/1938 | Schnase et al. . |
| 2,631,585 | 3/1953 | Siebrandt . |
| 2,698,483 | 1/1955 | Berkowitz . |
| 2,704,668 | 3/1955 | Park, Sr. . |
| 2,757,665 | 8/1956 | Tanikawa . |

(List continued on next page.)

FOREIGN PATENT DOCUMENTS 0 297 771  1/1989  European Pat. Off. .

OTHER PUBLICATIONS

H. Lipshitz et al., *Tappi Jounal*, pp. 237–245 (1990).

*Applied Medical Literature*.

Primary Examiner—John P. Leubecker
Attorney, Agent, or Firm—David G. Conlin; Peter F. Corless; Christine C. O'Day

[57] ABSTRACT

Grasping devices and articles exhibit enhanced gripping or holding power to a variety of surfaces, including surfaces that are slippery or otherwise difficult to hold. The invention involves in some aspects the discovery and use of gripping materials that have the unexpected enhanced capability to provide enhanced holding power to a variety of surfaces, including surfaces that are wet, slippery or otherwise potentially difficult to manipulate effectively, or surfaces on which it may be difficult to maintain an effective grip or traction. The gripping material is smooth and has a relative surface area roughness of between about 1.03 and about 10.5.

33 Claims, 6 Drawing Sheets

U.S. PATENT DOCUMENTS

| | | |
|---|---|---|
| 3,503,396 | 3/1970 | Pierie et al. . |
| 3,746,002 | 7/1973 | Haller . |
| 3,868,957 | 3/1975 | Doddington . |
| 3,892,241 | 7/1975 | Leveen . |
| 3,916,908 | 11/1975 | Leveen . |
| 3,921,640 | 11/1975 | Freeborn . |
| 3,977,410 | 8/1976 | Huston et al. . |
| 4,012,855 | 3/1977 | Gardner . |
| 4,016,883 | 4/1977 | Wright, Jr. . |
| 4,106,508 | 8/1978 | Berlin . |
| 4,122,856 | 10/1978 | Mosior et al. . |
| 4,165,747 | 8/1979 | Bermant . |
| 4,204,532 | 5/1980 | Lind et al. . |
| 4,274,415 | 6/1981 | Kanamoto et al. . |
| 4,324,248 | 4/1982 | Perlin . |
| 4,326,006 | 4/1982 | Kaminstein . |
| 4,337,774 | 7/1982 | Perlin . |
| 4,390,019 | 6/1983 | LeVeen et al. . |
| 4,478,219 | 10/1984 | Rozario et al. . |
| 4,531,519 | 7/1985 | Dunn et al. . |
| 4,571,390 | 2/1986 | Sakagami et al. . |
| 4,586,501 | 5/1986 | Claracq . |
| 4,708,140 | 11/1987 | Baron . |
| 4,735,843 | 4/1988 | Noda . |
| 4,777,950 | 10/1988 | Kees, Jr. . |
| 4,816,328 | 3/1989 | Saville et al. . |
| 4,836,205 | 6/1989 | Barrett . |
| 4,882,113 | 11/1989 | Tu et al. . |
| 4,917,960 | 4/1990 | Hornberger et al. . |
| 4,955,896 | 9/1990 | Freeman . |
| 4,973,609 | 11/1990 | Browne . |
| 4,976,721 | 12/1990 | Blasnik et al. . |
| 5,022,990 | 6/1991 | Doi et al. . |
| 5,026,382 | 6/1991 | Peiffer . |
| 5,028,332 | 7/1991 | Ohnishi . |
| 5,030,224 | 7/1991 | Wright et al. . |
| 5,037,457 | 8/1991 | Goldsmith et al. . |
| 5,079,272 | 1/1992 | Allegrezza, Jr. et al. . |
| 5,103,839 | 4/1992 | Schichman . |
| 5,133,724 | 7/1992 | Wilson, Jr. et al. . |
| 5,176,700 | 1/1993 | Brown et al. . |
| 5,217,802 | 6/1993 | Scarmoutzos . |
| 5,228,215 | 7/1993 | Bayer .......................................... 36/7.7 |
| 5,238,471 | 8/1993 | Blanchet-Fincher . |
| 5,238,547 | 8/1993 | Tsubouchi et al. . |
| 5,242,968 | 9/1993 | Minghetti et al. . |
| 5,254,131 | 10/1993 | Razi . |
| 5,257,558 | 11/1993 | Farzin-Nia et al. . |
| 5,258,005 | 11/1993 | Christian . |
| 5,286,382 | 2/1994 | Scarmoutzos et al. . |
| 5,308,271 | 5/1994 | Foulke . |
| 5,340,842 | 8/1994 | Adamski et al. . |
| 5,342,393 | 8/1994 | Stack . |
| 5,352,235 | 10/1994 | Koros et al. . |
| 5,356,466 | 10/1994 | Lawson . |
| 5,383,895 | 1/1995 | Holmes et al. . |
| 5,403,483 | 4/1995 | Hayashida et al. . |
| 5,405,618 | 4/1995 | Buttery et al. . |
| 5,439,476 | 8/1995 | Frantzides . |
| 5,527,340 | 6/1996 | Vogel . |
| 5,554,101 | 9/1996 | Matula et al. ....................... 600/204 X |
| 5,625,900 | 5/1997 | Hayes . |
| 5,658,307 | 8/1997 | Exconde . |
| 5,728,121 | 3/1998 | Bimbo et al. ........................... 606/207 |

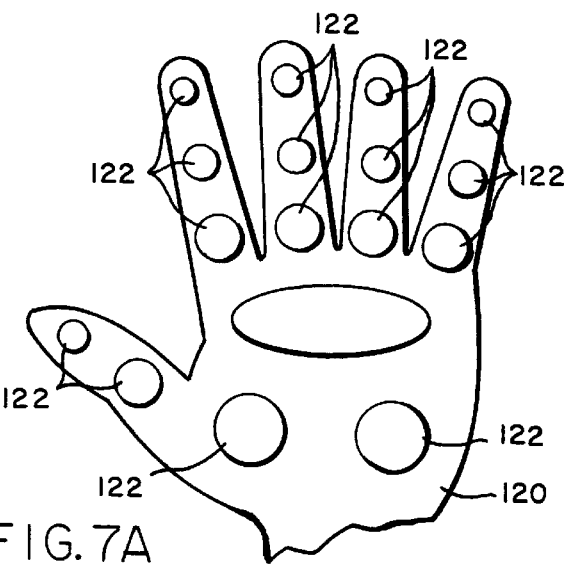
FIG.7A
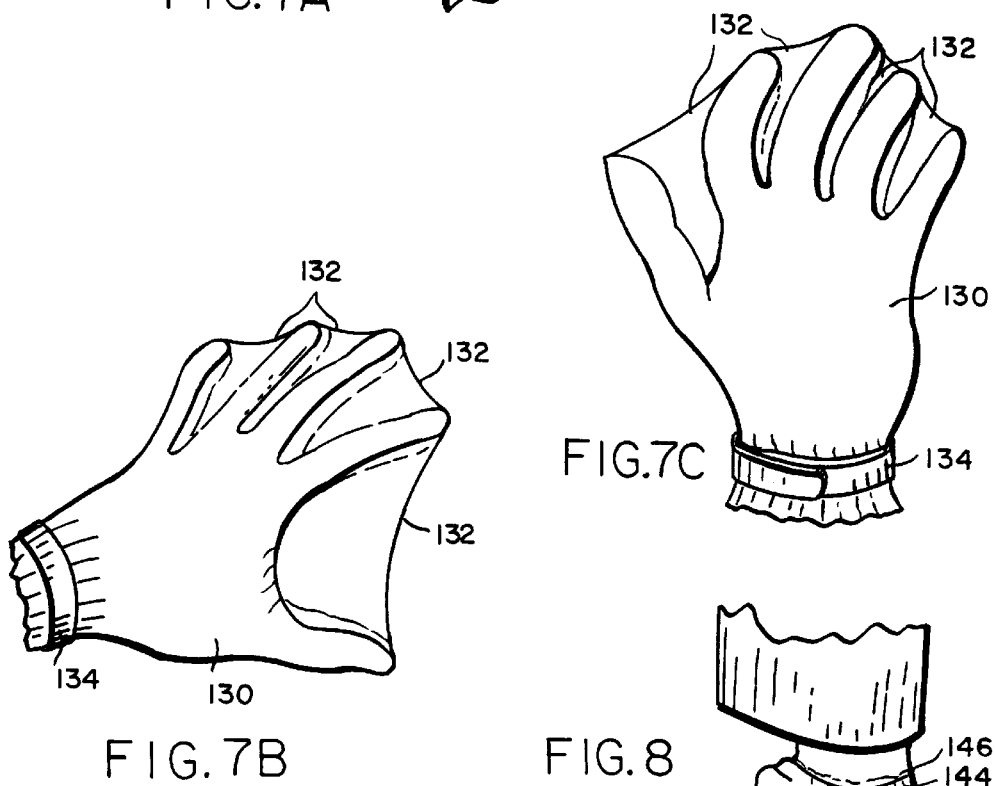
FIG.7B
FIG.7C
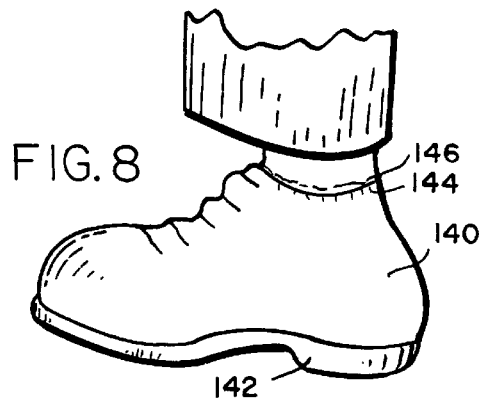
FIG.8

GRASPING DEVICES AND ARTICLES

This application is a continuation-in-part of U.S. application Ser. No. 08/726,617, filed Oct. 7, 1996, now abandoned.

BACKGROUND OF THE INVENTION

1. Field of the Invention

This invention relates to grasping devices and articles, including medical devices such as surgical dissectors, retractors and clamps, hand and foot coverings for medical and non-medical uses, and wrapping or covering materials such as hand and foot coverings to provide enhanced holding power on a variety of surfaces.

2. Background

In a wide variety of situations, it is necessary to grasp, grip and/or manipulate various articles that are difficult to hold onto as a result of smooth, wet or slippery grasp exposed surfaces, or surfaces that are otherwise difficult to grasp securely.

This is a particular issue in the medical area. For example, during medical procedures involving humans or animals, tissue is manipulated by a medical professional's hands or by various devices. More particularly, in traditional open surgeries, a surgeon's hands as well as surgical devices such as dissectors, retractors and graspers are employed. In the less invasive endoscopic procedures, such as laparoscopic and thoracoscopic surgeries, various surgical instruments including cutting, grasping and positioning instruments as well as viewing instruments are inserted into a relatively small incision to enable the physician to perform the surgery.

However, many prior medical grasping instruments have not provided satisfactory holding power to some types of tissue, thereby limiting their utility in various procedures or at a minimum complicating the surgeon's work. Tissue that must be manipulated during a surgical procedure can have relatively widely varying surface characteristics and can be highly slippery and difficult to grasp or move.

Such prior devices that provide limited holding power also may force the medical professional to use significant grasping pressure in order to manipulate the tissue as required to perform the surgical procedure. Use of such high grasping pressures can result in increased long-term trauma to tissue.

Additionally, prior endoscopic and other surgical grasping devices often may puncture, bruise or otherwise cause long-term trauma to the manipulated tissue. Such injury complicates and prolongs a patient's recovery and can impair the function of the damaged tissue. In some cases, the trauma can also substantially complicate the surgery in which it occurs. Indeed, if the trauma is severe, an additional procedure may be required to repair the damaged tissue. For example, a stomach wall tear may cause bleeding and/or perforation and require one or more stitches. In the case of removal of the gall bladder, if this organ is perforated, infected bile can leak into the abdominal cavity and cause an infection or other problems.

Non-surgical medical procedures also can require critical manipulation of tissue or other materials that are difficult grasp. For example, childbirth and other obstetrics procedures can require applying a secure yet atraumatic grip. Livestock birthing and other veterinary procedures also pose such grasping requirements.

The environments in which medical procedures are performed also present wet or otherwise slippery ground surfaces. In particular, the floors of operating rooms and the like are frequently wet. Medical personnel of course must be able to maintain good traction on such ground surfaces.

Moreover, many situations outside the medical area can involve grasping and manipulation of materials that are wet, slippery or otherwise difficult to hold. For example, processing and packaging of foodstuffs such as meats, seafoods and the like involve manipulation of materials that are often difficult to grasp. The ability to maintain good traction on slippery floor surfaces is also required in wet working environments such as food processing plants, cleaning facilities, etc. Ice covered surfaces also can necessitate the ability to maintain better traction than that provided by standard footwear. Poolside or dockside areas also can be slippery and pose hazards.

Also, in many instances, it can be important to maintain a secure grip on an object even if the object is not inherently exceedingly slippery or otherwise difficult to grasp. For example, various approaches have been adopted to improve a user's grip on tools, sports equipment and other objects. Moreover, even if an object is not inherently difficult to grasp securely, during use the object can become difficult to hold, such as when the object or user's hands become wet as a result of perspiration or rain or other precipitation. The ability to enhance a user's holding power on such objects would be a significant advance.

SUMMARY OF THE INVENTION

The present invention features novel grasping articles and surfaces that exhibit enhanced gripping or holding power to a variety of surfaces, including surfaces that are slippery or otherwise difficult to hold.

The invention involves in some aspects the discovery and use of gripping materials that have the unexpected enhanced capability to provide enhanced holding power or frictional characteristics to a variety of surfaces, including surfaces that are wet, slippery or otherwise potentially difficult to manipulate effectively, or surfaces on which it may be difficult to maintain an effective grip or traction. The gripping materials are especially useful in methods and articles of the invention for providing enhanced holding power between two surfaces where at least one of the surfaces is moist or wet or moisture or wetness is otherwise present between the two surfaces.

As discussed in detail below, the gripping materials can be a number of materials including polymeric and non-woven materials as well as sintered metals and other non-polymeric materials. Preferred gripping materials are substantially smooth (no significant visible protrusions by naked eye inspection as discussed more fully below) and exhibit a coefficient of friction of about 0.07 or greater.

The gripping materials of the invention impart enhanced holding power or gripping ability (e.g. absence of slippage) to a targeted surface relative to the holding power provided in the absence of the gripping material. Such enhanced holding power can be readily verified, e.g., by testing the ability of a device or article of the invention (that includes the gripping material) to grip a targeted object at a particular grasping pressure, relative to the ability of the same device or article but without the gripping material to grip the same object at the same grasping pressure.

In one aspect, the invention provides articles for use in the medical area including grasping devices of dissectors, clamps, retractors and forceps and pick-up devices as well as apparel for medical personnel such as surgical or birthing gloves to provide the medical professional a secure grip to tissue during surgery or other medical procedures such as child birthing. Foot coverings are also provided to maintain sure footing on the potentially slippery floor surfaces of operating rooms or other medical environments.

In further aspects, the invention provides articles suitable for use outside the medical area, including e.g. hand coverings to provide secure holds on slippery objects such as foodstuffs. The hand coverings of the invention also will be useful to lifeguards and others that require the ability to securely grasp wet or otherwise slippery objects. The invention also provides foot coverings that will provide enhanced traction on wet, ice-covered or other potentially slippery ground surfaces.

In additional aspects, the invention provides materials to enhance the ability to grasp securely a variety of objects including tools and sporting articles. In one preferred embodiment, the invention provides an encasing or covering material that can be conveniently applied to such objects. For example, the covering material of the invention can be applied as a wrap or tape to the handle of a tool or sporting article (e.g. racket handle or bicycle handle bars) to enable the user to more securely grasp the article, particularly under wet conditions.

Other aspects of the invention are disclosed infra.

BRIEF DESCRIPTION OF THE DRAWING

FIGS. 7A–7C show preferred hand coverings of the invention;

FIG. 8 shows a preferred foot covering of the invention; and

DETAILED DESCRIPTION OF THE INVENTION

Figure 1A:
FIGS. 1A–1B show a preferred dissector of the invention.
Figure 1B:
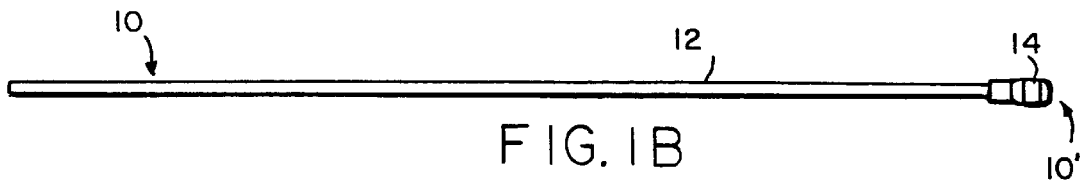

Referring now to the Drawings, where particularly preferred devices and articles of the invention are depicted, FIGS. 1A–1B show a surgical dissector 10 of the invention that has a generally elongate body 12 with a distal end 10' that incorporates ha gripping material 14 on its exposed surface. (In accordance with conventional practice regarding medical devices, "proximal end" designates the specified end closest to the medical personnel manipulating the device, and "distal end" designates the opposite end placed within a patient).

Gripping material 14 may be a separate material that at least partially covers or encases a portion of the dissector, typically the distal end. Gripping material 14 also may be an integral material of construction of the dissector, or the dissector may be subjected to a surface modification treatment to provide the desired gripping properties. Preferably material 14 covers or is incorporated into the dissector so that gripping material 14 is present on a sufficient amount of the exposed surface of a dissector to enable desired manipulations.

Gripping material 14 may be affixed or otherwise incorporated onto dissector 10 by any of a number of methods. For example, material 14 may be directly thermobonded or solvent bonded to a dissector if the dissector is formed of a polymer material that can form such a thermal or solvent bond. Material 14 also may be affixed to a dissector 10 by a suitable adhesive. The gripping material 14 also may be mechanically attached to a dissector such as by a clasp that circumscribes the dissector (e.g. around dilator neck 16) and holds an encasing sheet of the gripping material around a dissector end.

Gripping material 14 will facilitate use of dissector 10 by enabling effective manipulation of tissue as desired during the course of a surgical procedure. Prior dissectors of the type shown in FIGS. 1A–1B often may not manipulate tissue in an effective manner and require a surgeon to exert excessive pressure against the targeted tissue, or expend additional time to complete a procedure. Such enhanced pressure or additional surgical time can result in various complications and patient injuries.

Gripping material 14 suitably may be a variety of materials but should provide good holding power to a variety of tissue types in a wet environment as may be encountered during a surgical procedure. For example, preferred gripping materials provide good ability to manipulate tissue during orthopedic and other procedures where a dissector device is frequently used. Also, material 14 preferably provides good ability to manipulate tissue even after prolonged exposure to the wet environment of a surgical procedure, e.g. exposure for periods of 2 to 4 hours or more.

Gripping material 14 suitably may be a polymer, e.g. polyvinyldiene fluoride (PVDF); or a non-woven material, e.g. high-density polyethylenes such as TYVEK; or spun-bonded materials such as a polyester membrane material, e.g. Ahlstorm's 3283 product or Reemay's 2040 product; and the like. Non-polymeric materials also will be suitable, e.g. a sintered metal membrane. A sintered metal gripping material also may provide some mechanical benefits as a result of the fine rough surface of such materials. Suitable sintered metal membranes are commercially available from vendors such as Union Carbide.

Material 14 suitably may be either a hydrophilic or hydrophobic material provided the material maintains its gripping properties after being wetted out during use in a surgical procedure. However, hydrophobic materials will tend to be more durable in such wet environments and therefore will be generally preferred.

Gripping material 14 preferably will be a porous polymeric material or a non-woven material having a relative surface area roughness of between about 1.03 and 10.5, more preferably a relative surface area roughness of between about 1.08 and 4.5. See H. Lipshitz et al., *Tappi Journal*, pages 237–245 (October 1990), incorporated herein by reference, for a discussion of relative surface area roughness and the determination thereof. Preferred porous materials will have a pore size of about 200 microns or less, more preferably about 40 microns or less, preferably with a minimum size of about 0.05 microns. A particularly preferred gripping material is a PVDF material having a 2 micron pore size sold under the tradename of DURAPEL by the Millipore Corporation of Bedford, Massachusetts. The Reemay 2040 material (having about 10 micron pore size) is also a preferred gripping material.

Preferably, material 14 will exhibit a coefficient of friction of about 0.07 or greater, more preferably about 0.09 or greater, still more preferably about 0.6 or greater. Generally preferred materials will typically have a coefficient of friction of less than about 3, more typically less than about 2. The coefficient of friction of a particular material can be readily determined by standard procedures, specifically the sled test of the American Society for Testing and Materials (ASTM) Standard Test Method for Static and Kinetic Coefficients of Friction (test designation D 1894; modified to use sled on wet pig stomach tissue).

If desired, a material may be interposed between the gripping material and dissector unit. For example, a pad element layer formed from an elastomeric material as discussed more fully below with respect to clamp devices of the invention may be positioned under a gripping material 14 to avoid bruising or other trauma during use of the dissector.

A dissector of the invention can be use in the same manner as prior dissectors. For example, the dissector may be used to manipulate and remove intimal tissue. Also, the dissector may be used to manipulate a gall bladder as attached to a liver bed.

Figure 2A:
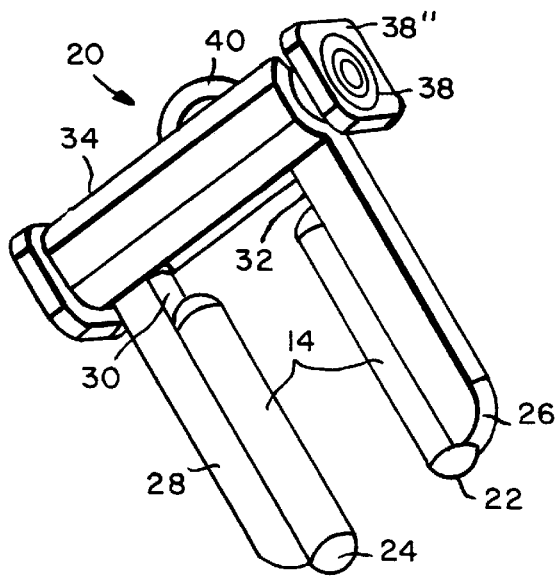
FIGS. 2A–2B show side views of a vascular clamp of invention in both an open position (FIG. 2A) and a closed position (FIG. 2B)
Figure 2B:
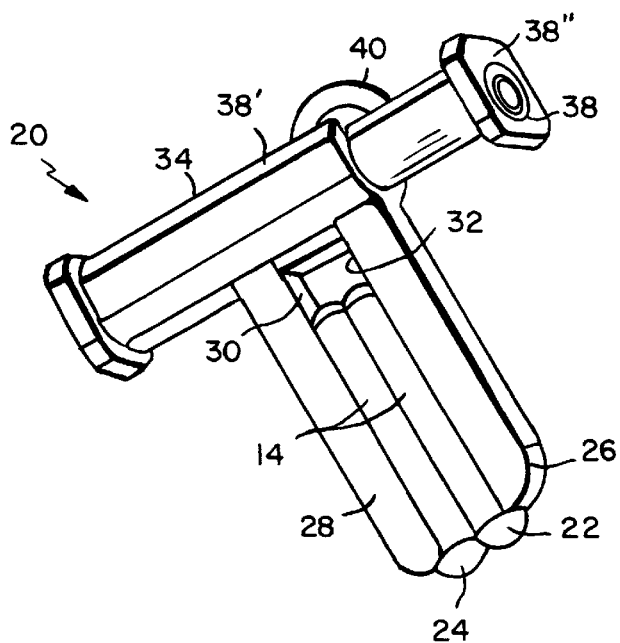

FIGS. 2A–2B shows a preferred surgical clamp 20 of the invention that includes a pair of clamp or grasping elements 22 and 24 disposed on support or clamp arm members 26 and 28 and that extend along the length of the respective support member. Preferably, each grasping element 22 and 24 is formed of a relatively soft material to avoid bruising or other trauma to manipulated (clamped) tissue during use of the device. A rubber or thermoplastic elastomeric material is particularly preferred for construction of the grasping elements, especially the material sold under the tradename of DYNAFLEX D-series (styrene-butadiene elastomer sold by GLS Co.). Also suitable will be material sold under the name of DYNAFLEX G-series (styreneethylene/butylene-styrene copolymer sold by GLS Co.). Other thermoplastic elastomers also will be suitable including C-flex, SANPREN and the like. Additional acceptable materials for forming a clamp element 22 or 24 include silicones, latex and other man-made rubber materials.

As least one and preferably both pad elements 22 and 24 incorporate the above-described gripping material 14 on at least a portion of the element's exposed and opposing surface. In similar fashion as discussed above with respect to dissector 10, gripping material 14 may be a separate material that at least partially covers or encases one or both of the clamp elements 22 and 24, gripping material 14 may be an integral material of construction of an element 22 or 24, or the preformed clamp pad may be subjected to a surface modification treatment to provide the desired gripping properties. As should be clear, references throughout the present disclosure to gripping material of reference numeral 14 designate the gripping material 14 as discussed above with respect to the dissector of FIGS. 1A and 1B. Thus, the above discussion regarding suitable materials 14, including material characteristics, methods for securing the gripping material to a surface of the device, suitable surface coverage provided by the gripping material and the like are all equally applicable to use of gripping material 14 on grasping elements 22 and 24.

Preferably the gripping material 14 covers or is incorporated into a clamp element 22, 24 so material 14 is present on a sufficient amount of the exposed surface of the clamp pad to provide the desired holding effect. The invention also includes clamp devices that do not comprise such elements 22 or 24, and where gripping material is incorporated into a portion of one or both of clamp opposed faces 30 and 32.

Clamp 20 suitably includes a spring (not shown) disposed within the hollow interior of the handle member 34 and between the handle member closed end 36 and first end 38' of the plunger 38 within clamp 20. When a force is applied to the plunger second end 38", the plunger slides further into the handle member. With plunger 38 fully depressed, as shown in FIG. 2A, the clamp 20 is in its open position and released from an artery or other tissue. When pressure is released from plunger end 38", the internal spring acts on plunger first end 38' to place clamp 20 in a closed position (i.e., the clamp elements 22 and 24 contact each other) as generally shown in FIG. 2B. Clamp 10 also preferably includes loop 40 for a keeper string to secure the clamp during a surgical procedure. The clamp also may be suitably white or other bright color for easy visibility and preferably is radiopaque.

The clamp components, other than elements 22 and 24 and gripping material 14, may be suitably formed of a variety of materials, e.g. a rigid plastic such as a polyethylene or a polypropylene, or a metal such as stainless steel, although a plastic material is generally preferred.

It also should be appreciated the gripping material 14 on the surface of a grasping element or other use as disclosed herein is preferably substantially smooth and provides good gripping properties without the type of visible (naked eye) protrusions reported in certain prior clamp systems. See for instance European Application 256966 (reports VELCRO surface) and U.S. Pat. No. 3,746,002 (reports surface pin members that puncture clamped tissue). Among other things, such protrusions could result in significant trauma to manipulated tissue. References herein to a substantially smooth surface of a gripping material 14 are intended to exclude those visible protrusions.

Figure 3A:
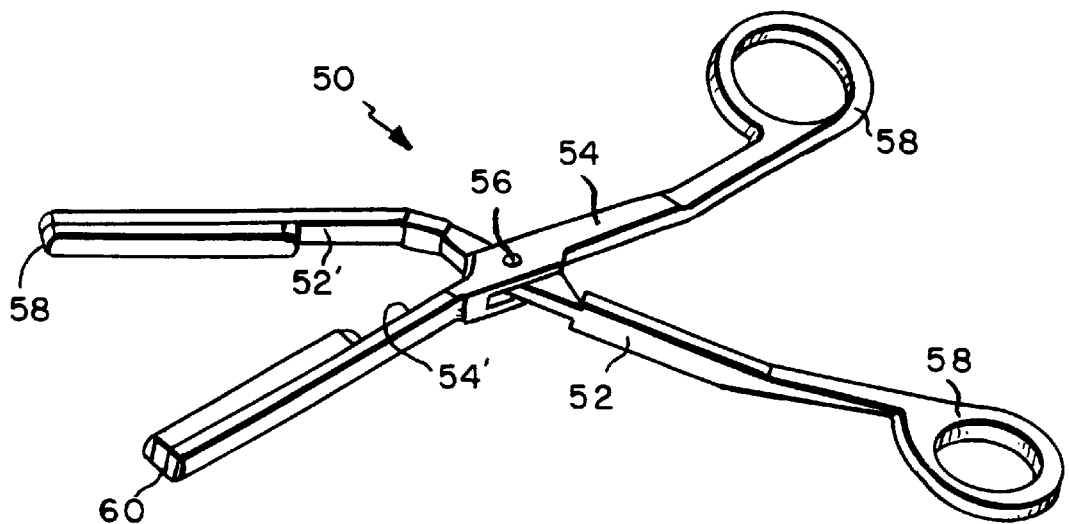
FIGS. 3A–3B show side view of a further preferred vascular clamp of the present invention.
Figure 3B:
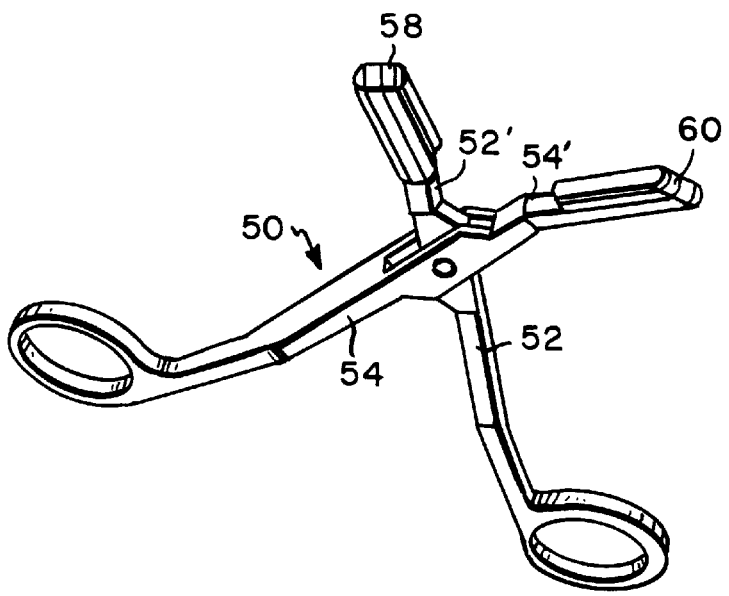

FIGS. 3A and 3B depict another preferred surgical clamp 50 of the invention that is a generally elongate structure with arms 52 and 54 that are preferably pivotally mounted at pivot point 56 to position arms 52 and 54 in an opposed facing relationship. The clamp proximal end preferably includes thumb and finger rings 58 to facilitate manipulation of the device. Rings 58 may be releasably secured in a desired position by connecting ratchet racks (not shown). Other mechanisms than the pivot engagement shown in FIGS. 3A–3B may be employed to activate arms 52 and 54 alone or in combination to enable grasping of a targeted object. For example, a single action system could be employed where one of the arms remains stationary and the other grasping arm moves toward and away from that stationary arm.

The distal ends of arms 52 and 54 include gripping material 14 as discussed above with respect to dissector 10 and clamp 20. While gripping material 14 may be incorporated directly onto an arm interior surface 52' or 54', preferably a grasping element 58 or 60 is positioned on such surfaces 52' and 54' and gripping material 14 is incorporated into exposed surfaces of one or both of such grasping elements 58 and 60. Grasping elements 58 and 60 are preferably formed of a relatively soft material to avoid bruising or other trauma to manipulated (clamped) tissue during use of the device as discussed above with respect to pads 22 and 24 of clamp 20. Thus, a rubber or thermoplastic elastomeric material is particularly preferred, especially the material sold under the tradename of DYNAFLEX D-series (styrene-butadiene elastomer sold by GLS Co.). Other suitable materials will include material sold under the name of DYNAFLEX G-series (styrene-ethylene/butylene-styrene copolymer sold by GLS Co.); other thermoplastic elastomers such as C-flex, SANPREN and the like; and other materials such as silicones, latex and other man-made rubber materials.

The clamp 50 structure itself is preferably formed of stainless steel, although the device also may be suitably formed of a rigid plastic or other materials if desired.

In preferred aspects, at least some clamps of the invention such as those exemplified in FIGS. 3A–3B are reusable, i.e. the clamp can be used in multiple surgical procedures. Specifically, for the device shown in FIGS. 3A–3B, grasping elements 58 and 60 can be removably attached to the device jaws or arms 52 and 54 and replaced after each medical procedure. In a particularly preferred embodiment, the grasping elements will be supplied separately from the clamp device, with the elements preferably packaged in sterile condition. The clamp device itself (without elements 58 and 60) can be cleaned to sterile condition after each use. Such a reusable system provides substantial cost and waste savings relative to a system that is entirely disposed of after a single use.

A grasping element, covered with gripping material 14, may be releasably attached to clamp arms by a variety of mechanisms to provide a reusable system. Preferred mechanisms permit snap-in attachment of a grasping pad element that can be readily performed by medical personnel and enable pad removal at the end of a medical procedure with minimal or no use of tools. For example, in preferred designs, elements 22 and 24 or 58 and 60 are each insert molded around a releasable lock component that can be releasably nested within the clamp arms. For instance, with respect to the system shown in FIGS. 3A and 3B, distal portions of arms 52 and 54 may include grooves in opposed faces 52' and 54' into which protruding ledges or latches of the grasping element lock component may fit to thereby secure the grasping element on the device.

Also, if desired, clamps of the invention may have grasping elements that are not readily removable or are permanently affixed and would not be removed before or after typical use of the device. Such devices may be disposable, i.e. the entire device is discarded after a single use, or the clamp device may be reusable wherein the entire clamp with grasping elements affixed thereon is cleaned and sterilized after use in a surgical procedure.

Figure 4A:
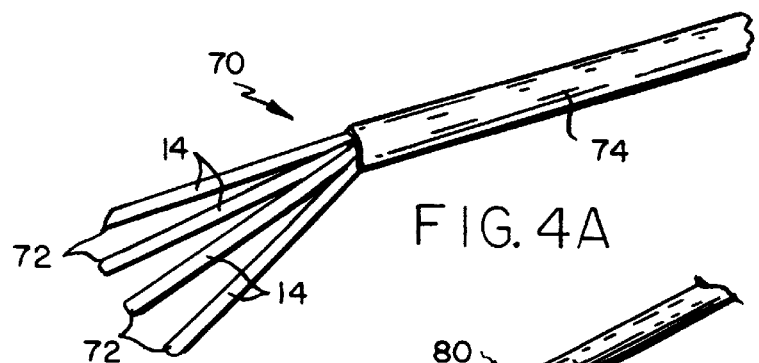
FIGS. 4A–4B show preferred retractors of the invention.
Figure 4B:
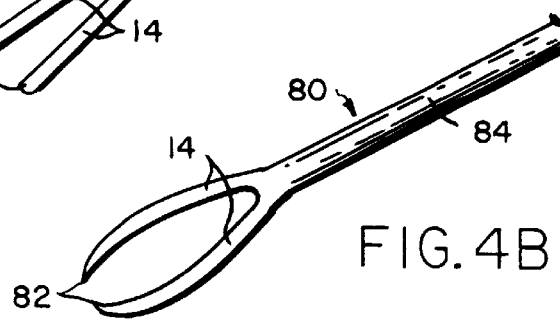

FIGS. 4A and 4B show selected surgical retractors of the invention. FIG. 4A shows fan-type retractor 70 which includes multiple retractor elements 72 extending from elongate body member 74. One or more of those elements includes gripping material 14 on at least one exposed side of the elements. FIG. 4B shows a further exemplary retractor 80 which also includes gripping material 14 on one or both of retractor elements 82 extending from an elongate body member 84.

Gripping material 14 may be incorporated onto retractor elements 72 or 82 by a variety of means including e.g. a mechanical or solvent bond attachment as discussed above with respect to clamp systems 20 and 50.

Use of gripping material 14 will facilitate manipulation and secure holding of tissue during use of the retractor. Prior retractors have suffered from the inability to provide a secure grip onto targeted tissue resulting in slippage, thereby interrupting the surgical procedure or even causing patient injury.

Figure 5A:
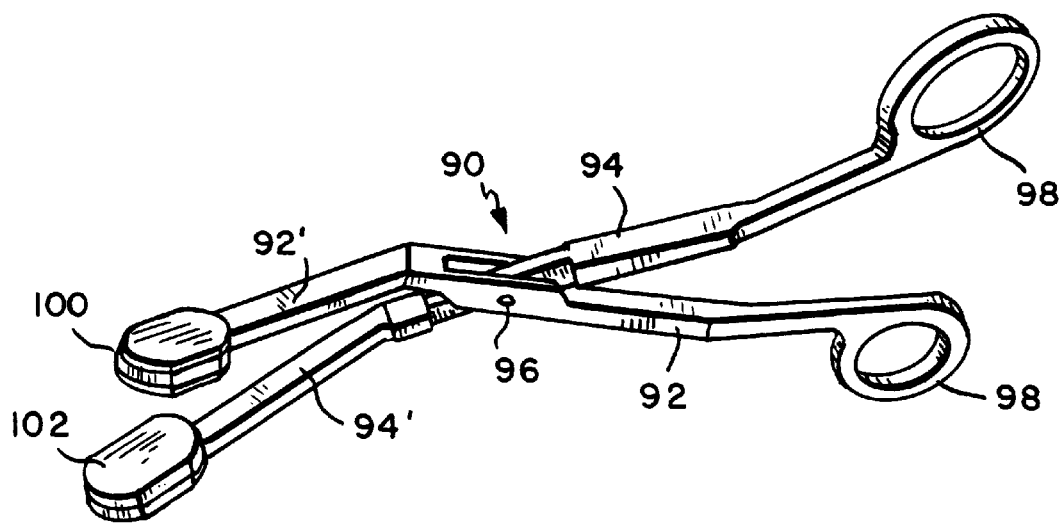
FIGS. 5A and 5B shows a preferred lung grasper of the present invention.
Figure 5B:
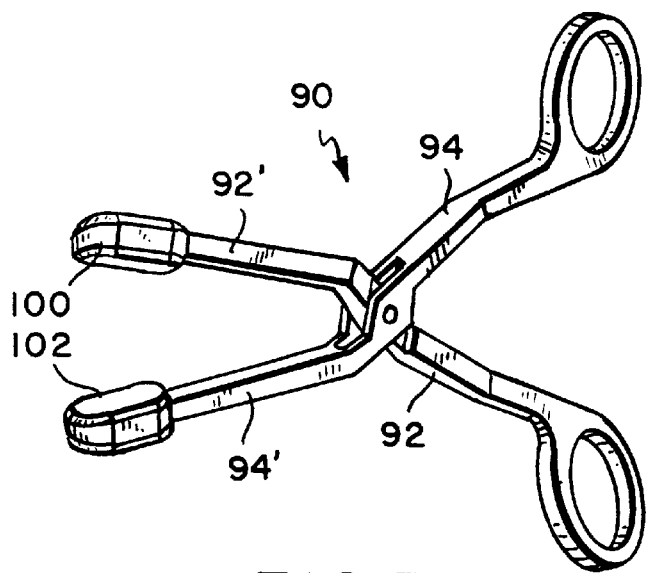

FIGS. 5A and 5B of the drawings shows a surgical grasper device of the invention specifically adapted for manipulations of a lung. Grasper 90 has arms 92 and 94 that are suitably pivotally mounted at pivot point 96. The grasper includes finger and thumb portions 98 or other manipulation system at the device's proximal end and a pair of opposed jaws or grasping elements 100 and 102 at the grasper's distal end. Rings 98 may be releasably secured in a desired position by connecting ratchet racks (not shown). As should be clear from FIGS. 5A–5B, relative movement of one or both of finger and thumb portions 98 cause similar relative movement of grasper arms 92 and 94. Arms 92 and 94 may have a variety of configurations and may include e.g. bent or angled portions as exemplified by the design shown in FIG. 5A to provide further control of the relative motion of the grasper arm distal ends. Other actuating mechanisms also can be employed. For example, a single action system could be employed, where one lung grasper arm remains stationary with the other grasping arm moving toward and away from that stationary arm.

Grasping elements 100 and 102 preferably are formed of relatively soft materials to avoid trauma to lung or other tissue during use. The materials discussed above for elements 22, 24, 58 and 60 of clamp systems 20 and 50 will be suitable, and especially preferred will be a rubber or thermoplastic elastomeric material such as the material sold under the tradename of DYNAFLEX D-series (styrene-butadiene elastomer sold by GLS Co.) or the material sold under the name of DYNAFLEX Gseries (styrene-ethylene/butylene-styrene copolymer sold by GLS Co.). The invention also includes grasper devices that do not contain such pad elements, and where the gripping material is incorporated into at least a portion of the grasper opposed faces 92' and 94'.

At least one and preferably both elements 100 and 102 incorporate a gripping material 14 on its exposed, opposing surface. In the same manner as discussed above with respect to grasper elements of clamps 20 and 50, the gripping material 14 may be a separate material that at least covers or encases one or both of the elements 100 and 102, material 14 may be an integral material of construction of elements 100 or 102, or the preformed elements 100 and 102 may be subjected to a surface modification treatment to provide the desired gripping properties. The abovediscussed preferred materials 14 are also preferred for use in a lung grasper of the invention.

Material 14 preferably covers or is incorporated into the element 100 or 102 so that gripping material 14 is present on at least about 50 or 70 percent or more of the entire exposed surface of the element, or even more preferably material 14 covers or otherwise is incorporated into essentially or completely the entire exposed surface of an element. References herein to "the exposed surface of a grasping element" indicate the grasping element surface not contacting or otherwise abutting opposed arm faces 92' and 94'.

Preferred lung graspers are reusable, and the graspers can be used in multiple surgical procedures with replacement of removably attached grasping elements 100 and 102. Preferably, a snap-in attachment is employed that can be readily performed by medical personnel and enable pad removal at the end of a medical procedure with minimal or no use of tools.

Such replaceable attachment of elements 100 and 102 may be accomplished by a variety of mechanisms, including use of the releasable attachments discussed above with respect to clamps 20 and 50, where elements 100 and 102 are insert molded around a lock component that includes side ledges or other protrusions which can fit within grooves on grasper arms 92 and 94.

The invention also includes medical device kits which comprise a dissector, clamp, retractor, grasper or other medical device of the invention supplied together with or separately from grasping elements with gripping material 14. Preferably the grasping elements will be packaged in a sterile condition, and two elements will be supplied in a given sterile packaging.

Figure 6A:
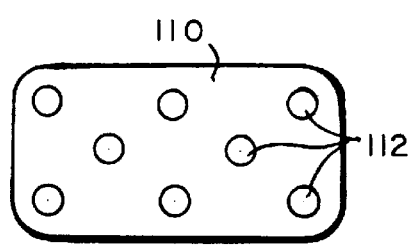
FIGS. 6A–6E show selected grasping elements of devices of the invention.
Figure 6B:
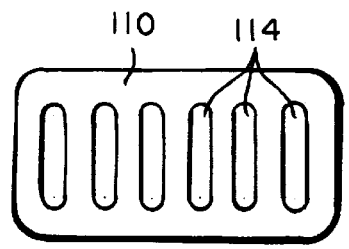
Figure 6C:
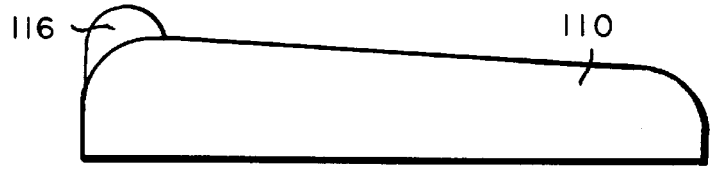
Figure 6D:
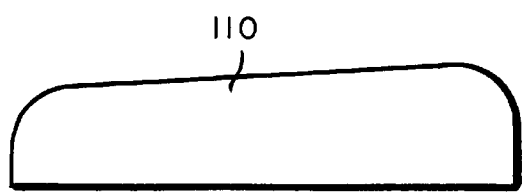
Figure 6E:
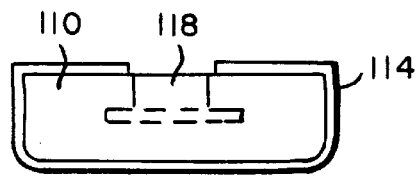

Grasping elements of devices of the invention generally may have a variety of configurations. Thus, a grasping element of a clamp, retractor or grasper of the invention may comprise topography to facilitate grasping. For example, as shown in FIG. 6 (which includes FIGS. 6A–6E), a grasping element 110 may have a series of raised bumps 112 as depicted in FIG. 6A, multiple ribs 114 as shown in FIG. 6B, one or more raised lips 116 as shown in FIG. 6C, or a relatively smooth surface as shown in FIGS. 6D and 6E. A downwardly sloping profile as generally shown in FIGS. 6C and 6D also may be preferred for certain applications. A grasping element with limited topography as shown in FIGS. 6D and 6E may be preferred for manipulation of a lung and other delicate organs such as liver. FIG. 6E also depicts a lock component 118 around which the grasping element 100 is insert molded as discussed above with respect to the exemplified clamp and grasper devices. Preferably, a grasping element is of a size sufficient to overlap or cover actuating arms of the device to avoid exposure of metal or other surfaces that could potentially pinch or otherwise cause trauma to the tissue being grasped and/or manipulated. Grasping elements used on clamps, graspers or other medical devices of the invention are preferably radiopaque to enable ready identification and location if an element inadvertently remains in a patient's body after surgery is completed.

As discussed above, the invention further includes hand coverings for medical and non-medical uses. The hand coverings of the invention in general contain exposed areas that include a gripping material 14 as discussed above. Typically, the glove or other hand covering of the invention will include gripping material 14 at least on the palm-side of the hand covering.

FIG. 7A shows a preferred glove 120 of the invention that includes selected exposed areas 122 containing a gripping material 14, specifically multiple patches 122 of gripping material 14 on each of finger, thumb and the palm portions of the glove. If desired, the entire exposed (exterior) area of the hand covering 120 may contain a gripping material 14, or at least a portion of the hand covering may contain a gripping material, such as one or more of the finger tips or the entire exposed palm-side area may contain a gripping material 14. The hand covering 120 may be formed from any of a wide variety of materials. For example, for use in surgical or other medical procedures, the hand covering may be suitably formed from a latex material, a spandex or other stretchable nylon, etc. For other applications, such as use in handling meats, seafoods or other foodstuffs, a non-stretchable nylon or other synthetic material may be preferred.

FIGS. 7B and 7C show a "webbed" hand covering 130 of the invention that includes connecting finger and thumb portions 132 and is particularly useful for persons working as lifeguards or other situations where swimming may be required. Gripping material 14 suitably covers at least portions of the palm-side of glove 130 as discussed above with respect to glove 120. The glove 130 may be suitably formed from any of a number of materials such as a lycra-spandex or other stretchable material, a nylon, natural materials such as a cotton, etc. The glove also may contain additional means to secure the article such as a wrist strap 134 with mating hoop and loop (VELCRO) attachment or the like.

FIG. 8 shows a foot covering or bootie 140 of the invention that suitably is worn over standard footwear. Bootie 140 includes gripping material 14 on at least portions of sole surface 142. The bootie is suitably formed from the same material as discussed above with respect to hand coverings 120 and 130. If desired an elastic band 134 can be disposed in the vicinity of the slipper upper edge 136. The elastic band can be affixed by any of a number of methods, for example by sewing or heat bonding the elastic bond on the foot covering, or by use of an adhesive. A bootie can be suitably secured on a user's foot or shoe by other mechanisms, e.g. if the bootie is formed of a spandex or other stretchable material, the bootie will stretch to conform around a user's foot. Laces or VELCRO straps also may be employed.

Footwear of the invention also can be provided by other methods, e.g. by affixing (such as by an adhesive) a patch of a gripping material 14 to the bottom of the heel or other bottom portions of a user's footwear, or by use of a sheet of material that contains a gripping material 14 that can be tied onto or otherwise affixed to cover at least portions of a user's conventional footwear.

Also, rather than being worn over or on a first set of footwear, foot coverings of the invention may be designed to be a person's sole footwear.

Footwear of the invention will be particularly suitable for use on and traversing an ice-covered surface such as a freezer area, ice rink, frozen body of water, outdoor areas in general such as sidewalks and the like during the winter season, etc. In such uses, footwear of the invention should substantially increase traction and grip on the ice-containing surface.

Footwear of the invention will be suitable for use on providing enhanced traction on wet surfaces, such as poolside or dockside areas or other ground surfaces that may be wet so that traction can be compromised.

Figure 9A:
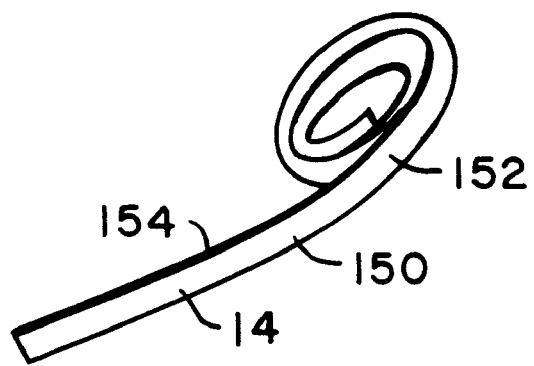
FIGS. 9A–9B show preferred covering materials of the invention.
Figure 9B:
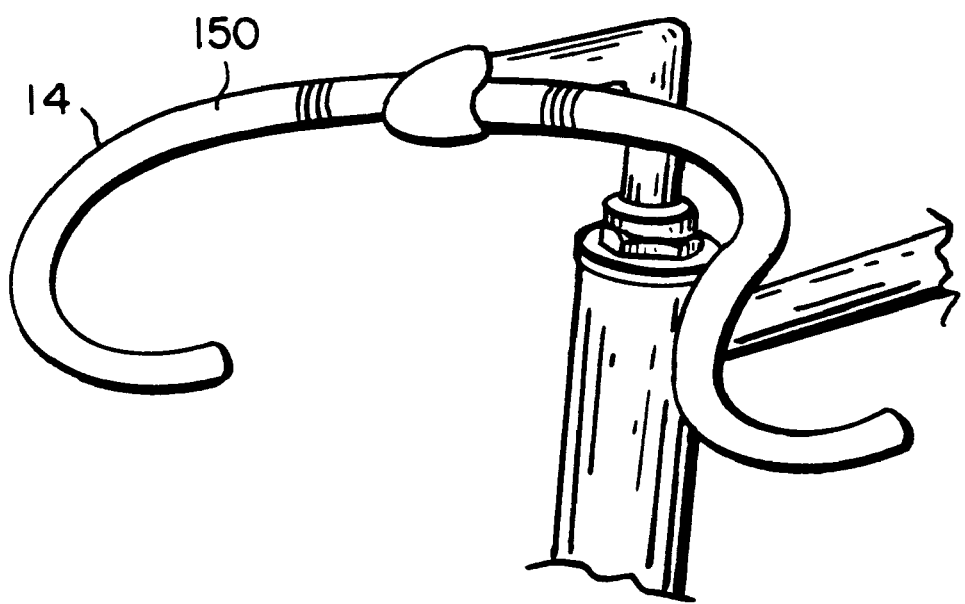

FIGS. 9A and 9B depict a covering or wrapping material 150 of the invention. That wrapping material 150 suitably includes a gripping material 14 on a first side 152 and preferably an adhesive backing on the opposed surface 154. The wrapping material 150 can be used for a wide variety of applications, including e.g. applying on the handles of tools or on sports equipment such as racket handles or bicycle handlebars as shown in FIG. 9B. The applied material will provide enhanced holding power, particularly in the presence of moisture as may be present from precipitation or perspiration.

A covering material of the invention that includes gripping material 14 may be used for a wide variety of other applications. For example, a covering material may be applied to the exposed surfaces of the nosepiece of eyeglasses to avoid slippage of the glasses.

Covering or wrapping material of the invention also is particularly useful in other situations where moisture or wetness may be present to provide enhanced gripping power under such wet or at least moist conditions.

The foregoing description is merely illustrative thereof, and it is understood that variations and modifications can be made without departing from the spirit or scope of the invention as set forth in the following claims.

What is claimed is:

1. A surgical dissector device comprising:
   an elongate body member, a substantially smooth gripping material having a relative surface area roughness of between about 1.03 and about 10.5 which is present on at least a portion of the surface of the dissector device, the gripping material providing enhanced holding power to a targeted surface relative to the dissector device in the absence of the gripping material.

2. The dissector device of claim 1 wherein the gripping material covers the distal end of the dissector device.

3. The dissector device of claim 1 wherein the gripping material has a coefficient of friction of about 0.6 or greater.

4. The dissector device of claim 1 wherein the gripping material is hydrophobic and porous.

5. A surgical clamp device comprising:
   first and second clamp arms positioned in an opposed relationship to enable grasping a targeted surface between the arms; and
   a substantially smooth gripping material having a relative surface area roughness of between about 1.03 and about 10.5 which is present on one or both of the arms, the material providing enhanced holding power to the targeted surface relative to the holding power provided by the elements in the absence of the gripping material.

6. The clamp device of claim 5 wherein the clamp arms are actuated by a plunger component.

7. The clamp device of claim 5 wherein the clamp comprises a handle at a proximal end and the arms are actuated around a pivot point.

8. The clamp device of claim 5 wherein the gripping material has a coefficient of friction of about 0.6 or greater.

9. The clamp device of claim 5 wherein the clamp comprises grasping elements attached to the first and second clamp arms, and the gripping material is incorporated into the exposed surface of one or both of the grasping elements.

10. The clamp device of claim 9 wherein the grasping elements are releasably attached to the clamp arms.

11. The clamp device of claim 9 wherein the grasping elements are permanently affixed to the grasping arms.

12. The clamp device of claim 5 wherein the device is reusable for multiple surgical procedures.

13. A surgical retractor device comprising:
    a plurality of elongate retractor elements, and a substantially smooth gripping material having a relative surface area roughness of between about 1.03 and about 10.5 which is present on at least a portion of the surface of one or more of the retractor elements, the gripping material providing enhanced holding power to a targeted surface relative to the retractor in the absence of the gripping material.

14. The retractor device of claim 13 wherein the gripping material has a coefficient of friction of about 0.6 or greater.

15. The retractor device of claim 13 wherein the gripping material is hydrophobic and porous.

16. The retractor device of claim 13 wherein the device is adapted for endoscopic use.

17. A hand or foot covering article comprising:
    an article having an end for inserting a user's hand or foot, a substantially smooth gripping material having a relative surface area roughness of between about 1.03 and about 10.5 which is present on at least portions of the outer exposed surface of the article, the gripping material providing enhanced holding power to a targeted surface relative to the article in the absence of the gripping material.

18. The article of claim 17 adapted for use in surgical procedures.

19. The article of claim 17 wherein the article is a hand covering article.

20. The article of claim 17 wherein the article is a foot covering article.

21. An article at least partially covered by a wrapping material, a surface of the wrapping material comprising a substantially smooth gripping material having a relative surface area roughness of between about 1.03 and about 10.5 that provides enhanced holding power to the article relative to the article in the absence of the gripping material, and wherein the gripping material is formed from a non-woven or polymeric or porous material.

22. The article of claim 21 wherein the gripping material is substantially smooth and has a coefficient of friction of about 0.6 or greater.

23. The article of claim 21 wherein the wrapping material at least partially covers a tool handle.

24. The article of claim 21 wherein the wrapping material at least partially covers a sporting article.

25. A method for providing enhanced holding power between two surfaces, comprising applying to at least one of the surfaces a gripping material, the gripping material providing enhanced holding power between the two surface relative to the holding power provided in the absence of the gripping material, and the gripping material being formed from a substantially smooth non-woven or polymeric or porous material having a relative surface area roughness of between about 1.03 and about 10.5 and having a coefficient of friction of about 0.07 or greater.

26. The method of claim 25 wherein moisture is present between the two surfaces and the gripping material provides enhanced holding power between the two surfaces in the presence of moisture.

27. The method of claim 25 wherein the gripping material is substantially smooth and has a coefficient of friction of about 0.6 or greater.

28. The surgical dissector device of claim 1, wherein the substantially smooth gripping material has a relative surface area roughness of between about 1.08 and about 4.5.

29. The surgical clamp device of claim 5, wherein the substantially smooth gripping material has a relative surface area roughness of between about 1.08 and about 4.5.

30. The surgical retractor device of claim 13, wherein the substantially smooth gripping material has a relative surface area roughness of between about 1.08 and about 4.5.

31. The hand or foot covering article of claim 17, wherein the substantially smooth gripping material has a relative surface area roughness of between about 1.08 and about 4.5.

32. The article of claim 21, wherein the substantially smooth gripping material has a relative surface area roughness of between about 1.08 and about 4.5.

33. The method of claim 25, wherein the substantially smooth gripping material has a relative surface area roughness of between about 1.08 and about 4.5.

* * * * *